US011110009B2

(12) United States Patent
Becker et al.

(10) Patent No.: US 11,110,009 B2
(45) Date of Patent: Sep. 7, 2021

(54) WELDING HELMET FOR DETECTING ARC DATA

(71) Applicant: ILLINOIS TOOL WORKS INC., Glenview, IL (US)

(72) Inventors: William J. Becker, Manitowoc, WI (US); Kyle A. Pfeifer, Appleton, WI (US); Eric T. Sommers, Appleton, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 409 days.

(21) Appl. No.: 15/425,534

(22) Filed: Feb. 6, 2017

(65) Prior Publication Data

US 2017/0143549 A1 May 25, 2017

Related U.S. Application Data

(63) Continuation of application No. 13/775,563, filed on Feb. 25, 2013, now Pat. No. 9,566,192.

(Continued)

(51) Int. Cl.
*A61F 9/06* (2006.01)
*B23K 37/00* (2006.01)
(Continued)

(52) U.S. Cl.
CPC ............... *A61F 9/067* (2013.01); *A61F 9/06* (2013.01); *B23K 9/16* (2013.01); *B23K 9/322* (2013.01);
(Continued)

(58) Field of Classification Search
CPC ...... A61F 9/06–068; B23K 9/322; F16P 1/06; G06F 3/005
(Continued)

(56) References Cited

U.S. PATENT DOCUMENTS

| 4,093,844 A | 6/1978 | Fellure |
| 4,721,947 A | 1/1988 | Brown |

(Continued)

FOREIGN PATENT DOCUMENTS

| CN | 2114441 | 9/1992 |
| CN | 101224519 | 7/2008 |

(Continued)

OTHER PUBLICATIONS

Alaro, Sadek C.A., et al.; "Emission Spectrometry Evaluation in Arc Welding Monitoring System," Journal of Material Processing Technology, vol. 179, pp. 219-224, Mar. 2006.

(Continued)

*Primary Examiner* — Erin E McGrath
(74) *Attorney, Agent, or Firm* — McAndrews, Held & Malloy, Ltd.

(57) ABSTRACT

A welding helmet for detecting arc data is provided. One embodiment of the welding helmet includes an arc detection system configured to detect one or more welding arcs that occur during one or more welding operations. The welding helmet also includes control circuitry configured to count a number of the one or more welding arcs detected by the arc detection system. The welding helmet includes a storage device configured to store the number of the one or more welding arcs.

22 Claims, 3 Drawing Sheets

Related U.S. Application Data (60) Provisional application No. 61/643,014, filed on May 4, 2012.

(51) Int. Cl.
  *B23K 9/16* (2006.01)
  *F16P 1/06* (2006.01)
  *B23K 9/32* (2006.01)
  *G06F 3/00* (2006.01)
  *G06F 3/01* (2006.01)

(52) U.S. Cl.
  CPC .............. *B23K 37/006* (2013.01); *F16P 1/06* (2013.01); *G06F 3/005* (2013.01); *G06F 3/012* (2013.01)

(58) Field of Classification Search
  USPC .................................................... 219/130.01
  See application file for complete search history.

(56) References Cited

U.S. PATENT DOCUMENTS

| | | | |
|---|---|---|---|
| 6,051,805 A * | 4/2000 | Vaidya | ................ B23K 9/0953 219/130.01 |
| 6,242,711 B1 | 6/2001 | Cooper | |
| 6,271,500 B1 | 8/2001 | Hirayama | |
| 6,583,386 B1 | 6/2003 | Ivkovich | |
| 7,304,269 B2 | 12/2007 | Fulmer | |
| 2003/0035233 A1 | 2/2003 | Jalili | |
| 2005/0001155 A1* | 1/2005 | Fergason | ................ A61F 9/067 250/221 |
| 2008/0189006 A1 | 8/2008 | Meehan | |
| 2008/0245775 A1 | 10/2008 | Opderbecke | |
| 2009/0094721 A1 | 4/2009 | Becker | |
| 2009/0173726 A1 | 7/2009 | Davidson | |
| 2009/0231423 A1 | 9/2009 | Becker | |
| 2009/0234483 A1 | 9/2009 | Leko | |
| 2009/0298024 A1 | 12/2009 | Batzler | |
| 2010/0217440 A1 | 8/2010 | Lindell | |
| 2011/0156989 A1 | 6/2011 | Huh | |
| 2011/0192828 A1 | 8/2011 | Dangelo | |
| 2011/0251838 A1 | 10/2011 | Huh | |

FOREIGN PATENT DOCUMENTS

| | | |
|---|---|---|
| CN | 101977720 | 2/2011 |
| CN | 102848050 | 1/2013 |
| GB | 2151777 | 7/1985 |

OTHER PUBLICATIONS

International Search Report from PCT application No. PCT/US2013/039187 dated Jul. 31, 2013, 10 pgs.

\* cited by examiner

WELDING HELMET FOR DETECTING ARC DATA

CROSS REFERENCE TO RELATED APPLICATIONS

This application is a Continuation of U.S. patent application Ser. No. 13/775,563, entitled "Welding Helmet for Detecting Arc Data", filed Feb. 25, 2013, which is a Non provisional U.S. Patent Application of U.S. Provisional Patent Application No. 61/643,014, entitled "Welding Helmet for Detecting Arc Data", filed May 4, 2012, both of which are hereby incorporated by reference in their entireties for all purposes.

BACKGROUND

The invention relates generally to welding helmets and, more particularly, to a welding helmet for detecting arc data.

Welding is a process that has increasingly become utilized in various industries and applications. Such processes may be automated in certain contexts, although a large number of applications continue to exist for manual welding operations. In both cases, such welding operations rely on a variety of types of equipment to ensure the supply of welding consumables (e.g., wire feed, shielding gas, etc.) is provided to the weld in appropriate amounts at the desired time.

Welding operations are often performed with goggles and/or helmets for protection of the operator. These helmets may include a face plate (or lens) that is darkened to prevent or limit exposure to the arc light. In some helmets, the lens is constantly dark with the user flipping down the helmet during welding. In other helmets, the lens may change from a clear state to a darkened state.

BRIEF DESCRIPTION

In one embodiment, a welding helmet includes an arc detection system configured to detect one or more welding arcs that occur during one or more welding operations. The welding helmet also includes control circuitry configured to count a number of the one or more welding arcs detected by the arc detection system. The welding helmet includes a storage device configured to store the number of the one or more welding arcs.

In another embodiment, a welding helmet includes an arc detection system configured to detect welding arcs that occur during one or more welding operations. The welding helmet also includes control circuitry configured to determine a duration of each welding arc of a portion of the welding arcs detected by the arc detection system. The welding helmet includes a storage device configured to store a total duration of the portion of the welding arcs detected by the arc detection system. The total duration of the portion of the welding arcs detected by the arc detection system includes a sum of the duration of each welding arc of the portion of the welding arcs.

In another embodiment, a welding helmet includes an arc detection system configured to detect one or more welding arcs that occur during one or more welding operations. The welding helmet also includes control circuitry configured to determine a resettable duration of the one or more welding arcs detected by the arc detection system. The welding helmet includes a storage device configured to store the resettable duration of the one or more welding arcs detected by the arc detection system, a first date that provides a reference point relating to when the resettable duration was last reset, a first time that provides the reference point relating to when the resettable duration was last reset, a second date that provides the reference point relating to when the resettable duration was last zero, a second time that provides the reference point relating to when the resettable duration was last zero, or some combination thereof.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present disclosure will be described below. These described embodiments are only examples of the present disclosure. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Welding helmets, such as helmets including auto-darkening welding lenses, include arc detection system that detect when a welding arc occurs during a welding operation, for example, by employing an optical sensor. Upon detection of the welding arc, the lens is darkened to a predetermined shade, thereby protecting the operator's eyes from the bright light emitted from the welding arc. Embodiments of the present disclosure obtain arc data using the arc detection system. For example, a welding helmet may count a number of welding arcs detected by the arc detection system. As another example, a welding helmet may determine a duration of each welding arc detected by the arc detection system.

Figure 1:
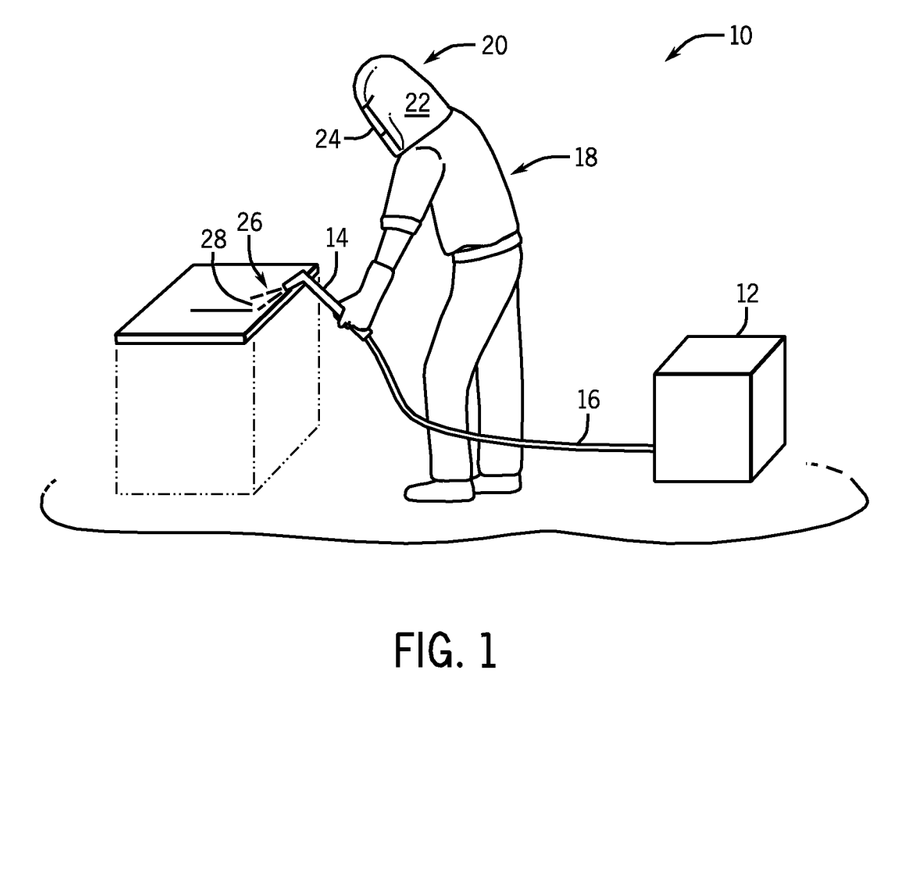
FIG. 1 is an illustration of an embodiment of a welding system including a welding helmet for determining arc data in accordance with aspects of the present disclosure.

Embodiments of the present invention may be used in a variety of welding applications. For example, FIG. 1 illustrates an arc welding system 10. As depicted, the arc welding system 10 may include a power supply 12 that generates and supplies welding power to an electrode 14 via a conduit 16. In the arc welding system 10, a direct current (DC) or alternating current (AC) may be used along with the consumable or non-consumable electrode 14 to deliver current to the point of welding. In such a welding system 10, an operator 18 may control the location and operation of the electrode 14 by positioning the electrode 14 and triggering the starting and stopping of the current flow.

In welding operations employing the welding system 10 depicted in FIG. 1, welding may be performed with certain precautions due to the generation of heat and bright light in the visible and non-visible spectra. To avoid overexposure to such light, a helmet assembly 20 is worn by the welding operator 18. The helmet assembly 20 includes a helmet shell 22 and a lens assembly 24 that may be darkened to prevent or limit exposure to the light generated by a welding arc 26.

When the operator 18 begins the welding operation by applying power from the power supply 12 to the electrode 14, the welding arc 26 is developed between the electrode 14 and a work piece 28. The electrode 14 and the conduit 16 thus deliver current and voltage sufficient to create the welding arc 26 between the electrode 14 and the work piece 28. The welding arc 26 melts the metal (the base material and any filler material added) at the point of welding between the electrode 14 and the work piece 28, thereby providing a joint when the metal cools. The welding system 10 may be configured to form a weld joint by any known technique, including shielded metal arc welding (SMAW) (i.e., stick welding), metal inert gas welding (MIG), tungsten inert gas welding (TIG), gas welding (e.g., oxyacetylene welding), and/or resistance welding.

As described below, the helmet assembly 20 used in the welding system 10 includes the lens assembly 24 that transitions between a clear state and a darkened state. Generally, the lens assembly 24 may include electronic components which cause the lens to darken (e.g., an LCD that darkens when a voltage is applied across the layer). For example, the operator 18 may "turn on" the lens assembly 24 to provide a voltage across the lens and associated electronic components, thereby causing the assembly 24 to transition from a light state (e.g., relatively clear state) to a darkened state.

In particular embodiments, the lens assembly 24 may include electronic components that cause the lens to automatically darken when sensors detect bright light in excess of a threshold value, for example, by triggering circuitry of the lens assembly 24 to provide a voltage across the lens. In some embodiments, the lens assembly 24 may include electronic components that cause the lens to automatically darken when sensors detect a sufficiently fast enough transition of light intensity (e.g., from non-welding to welding). In accordance with aspects of the present disclosure, the welding helmet assembly 20 may be configured to count a number and/or determine a duration of welding arcs 26 detected. As will be appreciated, using a number of welding arcs 26 and/or durations of welding arcs 26 performed by the welding operator 18, welding operations may be evaluated to improve welding technique and/or efficiency.

Figures 2, 3:
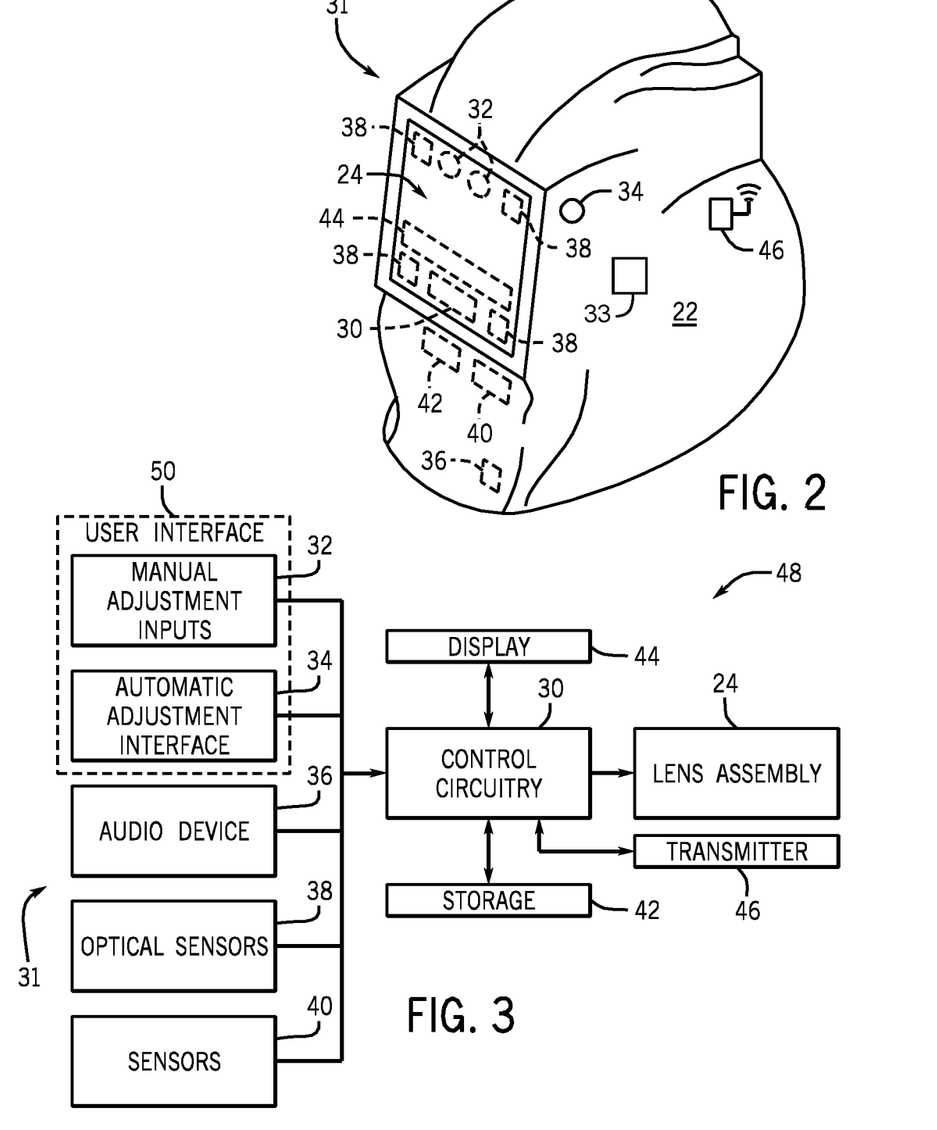
FIG. 2 is a perspective view of an embodiment of the welding helmet of FIG. 1 in accordance with aspects of the present disclosure.
FIG. 3 is a block diagram of an embodiment of the welding helmet of FIG. 2 in accordance with aspects of the present disclosure.

FIG. 2 is a perspective view of an embodiment of the helmet assembly 20 of FIG. 1. The helmet shell 22 may constitute the general frame and support for the components of the welding helmet assembly 20. For example, the helmet shell 22 provides a partial enclosure about the face and neck of the operator 18 to shield the operator 18 from exposure to the high heat and bright light produced during welding. In addition to providing general protection, the helmet shell 22 provides a location to mount the lens assembly 24, control circuitry 30 (e.g., hardware and/or software), and any additional accessories.

The control circuitry 30 may include circuitry configured to monitor and control the state of the lens assembly 24 (e.g., a lens control module), as well as circuitry (e.g., processor, microcontroller, internal real-time clock (RTC), etc.) to control other functions of the helmet assembly 20. For example, the control circuitry 30 may perform signal amplification, conditioning, filtering, or manipulation. As another example, the control circuitry 30 may be used to count a number and/or determine a duration of welding arcs 26 detected. In one embodiment, the control circuitry 30 may be provided as a component of the lens assembly 24. For example, the lens assembly 24 may be mounted to the helmet shell 22 as a single unit. In another embodiment, the control circuitry 30 may be a component that is separate from the lens assembly 24. For example, where the control circuitry 30 is separate from the lens assembly 24, it may be mounted remotely in the helmet shell 22 with a connection (e.g., via wire conductors, or wirelessly) to the lens assembly 24 sufficient to transmit control signals. In certain embodiments, the control circuitry 30 may acquire and process various inputs, compare the inputs to the values stored in a memory, and carry out programmed functionality to provide corresponding outputs to accessories related to the welding helmet assembly 20 (e.g., to lighten and darken the lens, extract data from sensors, determine arc data).

An arc detection system 31 is used to detect a welding arc 26 that occurs during a welding operation and provide data to the control circuitry 30. The arc detection system 31 may include various user interface inputs and sensor inputs. For example, user interface inputs may include one or more manual adjustment inputs 32 and an automatic adjustment interface 34. The manual inputs 32 may include inputs disposed inside or outside of the helmet shell 22 (e.g., coupled to the lens assembly 24) that provide signals when the inputs are manipulated by the operator 18. By disposing the manual inputs 32 within the helmet shell 22, the operator 18 may be discouraged from adjusting settings while the welding arc 26 is present. The manual inputs 32 may be any device which provides a signal in response to the input of the operator 18. For example, the manual inputs 32 may include digital encoders, knobs, potentiometers, touch-sensitive sensors, touchscreens, buttons (e.g., reset), keys, and so forth. Accordingly, the manual adjustment inputs 32 may enable the operator 18 to manually adjust helmet 20 settings. For example, in certain embodiments, the manual inputs 32 may enable the operator 18 to adjust clock settings, alarm settings, timer settings, arc-on time settings, alerts, enter a user identification (ID), enter a password, etc.

The welding helmet assembly 20 may include at least one audio device 36 (e.g., microphone, speaker, beeper, buzzer, etc.). In certain embodiments, the audio device 36 may be configured to pick up audible voice commands from the operator 18 so that settings to the lens assembly 24 may be adjusted hands-free. Audible commands may include adjusting the light sensitivity threshold, directing the lens to switch to the dark or clear state, adjusting data displayed by the welding helmet assembly 20 (e.g., welding arc duration, number of welding arcs 26), and so forth. In certain embodiments, the audio device 36 may provide audible feedback to the operator 18, such as audible alerts.

The arc detection system 31 may include optical sensors 38, which may be photodetectors configured to sense light (e.g., ultra violet (UV), visible, infrared (IR)) and/or non-optical sensors 40 (e.g., electromagnetic sensors configured to detect electromagnetic emissions). The optical sensors 38 may determine the intensity of the light experienced at the lens and output a signal indicative of the light intensity to the control circuitry 30. Based on the signal provided by the sensors 38, the control circuitry 30 may output a signal to the lens assembly 24 to change to the light or dark state. The auto-darkening lens may operate by comparing the detected light intensity to the sensitivity threshold. That is, the optical sensors 38 may be connected to an amplification and/or voltage biasing circuit which outputs a signal (e.g., voltage) directly related to the intensity of light detected by the optical sensors 38. This voltage is then compared to a threshold voltage (e.g., the sensitivity voltage), and the result of the comparison determines if the lens state should be dark or light.

In certain embodiments, the optical sensors 38 may include one or more cameras. As will be appreciated, the one or more cameras may be used to capture images. After capturing the images, the images may be processed real time (e.g., by the control circuitry 30) to determine whether features of the images indicate the presence of welding, grinding, cutting, and so forth. For example, the images may include bright spots, sparks, or other features that may indicate that welding, grinding, and/or cutting images have been captured. In some embodiments, camera data may be captured during a welding operation and post-processed after the welding operation is complete to determine one or more durations and/or counts related to welding arcs established during the welding operation.

The arc detection system 31 may include the non-optical sensors 40 for detecting a welding arc 26. For example, the non-optical sensors 40 may include UV sensors, IR sensors, RF antennas, or any suitable sensor that can detect electromagnetic emissions. By using optical sensors 38 and non-optical sensors 40, emissions from multiple regions of the electromagnetic spectrum (e.g., multiple wavelength ranges) may be detected. Detection and analysis of multiple emissions from a welding arc 26 may reduce and/or eliminate false detections of a welding arc 26 (e.g., false detections produced by a bright environment, such as outdoor sunlight, or flashing lights). For example, the arc detection system 31 may use emissions from two or more different regions of the electromagnetic spectrum to detect a welding arc 26 and thereby limit false detections.

As will be appreciated, when welding with different welding processes, emissions having different intensities and from different regions of the electromagnetic spectrum may be detected. Accordingly, the type of welding process may be detected using the optical sensors 38 and the non-optical sensors 40. For example, aluminum welding is typically brighter than welding with other materials. As another example, TIG welding often emits a high frequency (HF) emission when a welding arc 26 is initiated.

A welding arc 26 may be detected by the arc detection system 31 when the welding helmet assembly 20 is placed in close proximity to welding activity that is not being performed by the operator 18 wearing the helmet assembly 20. In order to detect only the welding arcs 26 that correspond to the operator 18 wearing the helmet assembly 20, the arc detection system 31 may use non-optical sensors 40. Such non-optical sensors 40 may include position sensors, orientations sensors, motion sensors, location sensors, temperature sensors, humidity sensors, sound level sensors, and so forth. For example, the sensors 40 may include thermistors, thermocouples, hygrometers, pressure transducers, piezoelectric sensors, tactile switches, geospatial locating devices (e.g., global positioning system (GPS) device), accelerometers, gyroscopes, magnetometers, and microelectromechanical systems (MEMS). As will be appreciated, the sensors 40 may be disposed at any location on, or in, the welding helmet assembly 20. For example, the sensors 40 may be within the lens assembly 24, on or in the helmet shell 22, on a headgear of the welding helmet assembly 20, and so forth.

Using such sensors 40, the arc detection system 31 may detect when the operator 18 wearing the welding helmet assembly 20 moves. The sensors 40 may detect such movement and use the movement to aid in determining whether a welding arc 26 is detected. For example, if movement of the operator 18 is not detected for a pre-determined period of time (e.g., ten seconds, sixty seconds) prior to emissions being detected from a welding arc 26, the detected emissions may be considered a false detection.

The arc detection system 31 may also detect emissions from a welding arc 26 while the operator 18 is wearing the welding helmet assembly 20 with the helmet 20 in the raised (e.g., up) position. The operator 18 may have the helmet 20 in the raised position while performing non-welding activities such as setting up for a welding application. Therefore, it may not be desirable to consider welding arcs 26 detected while the helmet 20 is in the raised position as being valid. Accordingly, sensors 40 may be used to detect whether the helmet 20 is in the raised position or the lowered (e.g., down) position. For example, a first accelerometer may be placed on the lens assembly 24 or helmet shell 22. A second accelerometer may be placed at another location within the welding helmet assembly 20 (e.g., headgear). By using data from the first and second accelerometer, the control circuitry 30 may determine whether the welding helmet assembly 20 is in the raised or the lowered position. In certain embodiments, the arc detection system 31 may consider detected emissions as false emissions unless the welding helmet assembly 20 is in the lowered position.

As will be appreciated, the non-optical sensors 40 may be used to detect a type of operation being performed. For example, the non-optical sensors 40 may be used to detect whether a welding operation, a cutting operation, and/or a grinding operation is being performed.

During operation, the control circuitry 30 obtains arc data that relates to the welding arcs 26 detected by the arc detection system 31. Specifically, the control circuitry 30 may determine a duration of welding arcs 26 detected by the arc detection system 31. For example, the control circuitry 30 may determine a duration of each welding arc 26 detected by the arc detection system 31. Using the duration of welding arcs 26 detected by the arc detection system 31, the control circuitry 30 may determine a total duration of welding arcs 26 that have occurred over a period of time. For example, the control circuitry 30 may determine a total duration of welding arcs 26 for the life of the lens assembly 24 or the welding helmet assembly 20. The control circuitry 30 may store a date and/or a time that corresponds to when the total duration of welding arcs 26 was last zero, or some other initial value. The control circuitry 30 may also determine a total duration of welding arcs 26 since a prior reset occurred. In such embodiments, the manual inputs 32 may be used to reset the total of welding arc 26 durations. The control circuitry 30 may store a date and/or a time that corresponds to when the reset occurred. The control circuitry 30 may also be used to determine a total duration of welding arcs 26 for a specific operator 18. For example, an operator 18 may be identified by being the sole operator of the welding helmet assembly 20 and/or the lens assembly 24. In welding applications where multiple operators use a single welding helmet assembly 20, an operator 18 may be identified (e.g., authenticated) by a user ID input into the welding helmet assembly 20, for example. Likewise, in welding applications where multiple operators use a single lens assembly 24, an operator 18 may be identified by a user ID input into the lens assembly 24, for example. The duration of welding arcs 26 performed by an operator 18 may be useful to determine productivity and efficiency of welding operations.

The control circuitry 30 may also count a number of welding arcs 26 detected by the arc detection system 31. For example, the control circuitry 30 may determine a total number of welding arcs 26 detected by the arc detection system 31 for the life of the lens assembly 24 or the welding helmet assembly 20. The control circuitry 30 may store a date and/or a time that corresponds to when the total number of welding arcs 26 was last zero, or some other initial value. The control circuitry 30 may also determine a total number of welding arcs 26 detected since a prior reset occurred. In such embodiments, the manual inputs 32 may be used to reset the total number of welding arcs 26 detected. The control circuitry 30 may store a date and/or a time that corresponds to when the reset occurred. The control circuitry 30 may also be used to determine a total number of welding arcs 26 for a specific operator 18. In certain embodiments, certain welding arcs 26 may not be included in the count of the number of welding arcs 26 detected by the arc detection system 31. For example, prior to welding two parts together, the operator 18 may tack weld the two parts together at various locations to align and connect the two parts. The tack welds may be a short duration (e.g., one to two seconds). Based on the duration of the weld, tack welds may be detected. The tack welds may not be included in the number of welding arcs 26 detected by the arc detection system 31. For example, if the tack welds have a duration less than a predetermined threshold, the tack welds may not be included in the number of welding arcs 26 detected by the arc detection system 31. As will be appreciated, the predetermined threshold may be adjusted by the operator 18 (e.g., via the inputs 32, 34). Furthermore, the tack welds may be excluded from the total arc weld duration. In addition, the tack welds may have a separate total tack weld duration and/or count that is determined by the control circuitry 30.

As will be appreciated, if tack welding is detected, the control circuitry 30 may be configured to control the lens assembly 24 based on a "tack mode" in which the lens assembly 24 darkens to a predetermined shade while tack welding is detected and lightens to a predetermined shade (e.g., typically darker than the lightest shade available) while no welding is detected. Because tack welding entails numerous quick changes in lens shade, using a darker non-welding shade may be easier on the operator's 18 eyes.

Various lens modes (e.g., weld, cut, grind) may be available for the lens assembly 24. Each of the lens modes may have different lens settings that may be stored in a storage device 42 (e.g., volatile memory, non-volatile memory). When the operator 18 switches between different modes, the lens settings for that mode may be applied to the lens assembly 24. Such lens settings may relate to shade options, sensor types, enabling sensors, disabling sensors, and so forth. In certain embodiments, the control circuitry 30 may determine a total duration and/or total number of welding arcs 26 for each available lens mode.

The control circuitry 30 may also determine a total duration and/or total number of welding arcs 26 based on data received from one or more of the sensors 38 and 40. For example, temperature and humidity sensors may be configured to measure a heat index of air within the welding helmet assembly 20. The accuracy and/or efficiency of a welding operation may be affected by the heat index. Therefore, the control circuitry 30 may determine a total duration and/or number of welding arcs 26 performed while the heat index of the air inside the welding helmet assembly 20 is greater than a predetermined threshold. As another example, location sensors may determine the location of the welding helmet assembly 20 (e.g., global geographical location, location within a manufacturing plant). The control circuitry 30 may determine a total duration and/or total number of welding arcs 26 that relate to a specific location or location range to track welding activity that occurs in the location or location range. It should be noted that while the total duration and/or total number of welding arcs 26 for a specific category, sensor, and/or location may be determined, an overall total duration and/or total number of welding arcs 26 may also be determined.

As a further example, accelerometers may determine an orientation of the welding helmet assembly 20 (e.g., flat—facing down while welding on a surface parallel to the ground, vertical or horizontal—facing straight ahead while welding on a surface perpendicular to the ground, overhead—facing upward while welding on a surface above the operator's head). The control circuitry 30 may determine a total duration and/or total number of welding arcs 26 that relate to a specific orientation of the welding helmet assembly 20.

The control circuitry 30 may be used to calculate additional data that relates to the welding arcs 26. For example, the control circuitry 30 may calculate an average weld duration for all welding arcs 26. The control circuitry 30 may also calculate an average weld duration for a specific category, such as welding orientation, welding process, lens mode, environmental conditions, location, tack welding, non-tack welding, and so forth. The control circuitry 30 may also determine a longest duration weld, a shortest duration weld, a most number of welds performed in a predetermined time period, and a least number of welds performed in a predetermined time period.

As discussed above, the welding helmet assembly 20 may include the storage device 42 to store data that relates to welding arcs 26 detected by the arc detection system 31. The storage device 42 may include volatile and/or non-volatile memory. However, it should be noted that to protect data in the event of loss of power (e.g., low battery voltage), the storage device 42 may be non-volatile memory. As will be appreciated, the storage device 42 may store any data sensed, detected, calculated, and/or determined. For example, the storage device 42 may store the cumulative total (non-resettable) duration of welding arcs 26 (e.g., the total may include the sum of the duration of each welding arc 26 detected by the arc detection system 31), the cumulative total (resettable) duration of welding arcs 26, the total duration of welding arcs 26 that relate to a particular sensor (e.g., the total may include the sum of the duration of each welding arc 26 detected by the arc detection system 31 since the last reset has occurred), the overall total number of welding arcs 26, the total number of welding arcs 26 that relate to a particular sensor, a non-resettable number of welding arcs 26, a welding arc 26 start time, a welding arc 26 end time, an overall average welding arc 26 duration, an average welding arc 26 duration for a particular sensor, a longest duration weld, a shortest duration weld, a most number of welds performed in a predetermined time period, a least number of welds performed in a predetermined time period, lens settings for each weld, sensor values for each weld, user IDs for each weld, durations of each welding arc 26 performed while a user is authenticated, and so forth. Accordingly, the storage device 42 may store a history of welding activity performed with the welding helmet assembly 20. The storage device 42 may include memory devices and/or interface devices (e.g., universal serial bus (USB), removable memory card slot, secure digital (SD) slot) for memory devices.

The welding helmet assembly 20 may include a display 44 configured to display welding arc 26 data received from the control circuitry 30 and/or the storage device 42. The display 44 may be a passive or active matrix liquid crystal display (LCD), seven-segment displays, one or more light emitting diodes (LEDs), an LED display, a touchscreen, or any other suitalbe type of display. For example, the display 44 may be emissive or reflective and may also backlit or frontlit. The display 44 may display the lens assembly 24 settings or any other type of information. In certain embodiments, the contents of the display 44 may be changed based on adjustments made using the inputs 32 and 34. In some embodiments, the language or format of displayed information may be selectable by the operator 18. In order to conserve battery life, the display 44 may be configured to automatically turn off when a welding arc 26 is detected. Furthermore, the display 44 may be built into the lens assembly 24, or the display 44 may be separate from the lens assembly 24.

In certain embodiments, the display 44 may be configured to show: an overall total duration of welding arcs 26, a total duration of welding arcs 26 since a previous reset, a duration of a welding arc 26 being performed (e.g., the duration of a welding arc 26 that has not ended), a duration of a previous welding arc 26 (e.g., the duration of a welding arc 26 that has already ended), a detected welding process, an overall total number of welding arcs 26, a total number of welding arcs 26 since a previous reset, a total number of welding arcs 26 for a shift, day, or week, an average welding duration, a longest welding duration, a shortest welding duration, a most number of welds performed in a predetermined time period, a fewest number of welds performed in a predetermined time period, and so forth. As will be appreciated, the display 44 may be configured to show information to the operator 18 before, after, and/or during a welding operation.

A welding operator 18 may receive an alert (e.g., feedback) from the display 44 and/or from the audio device 36. In certain embodiments, the welding operator 18 may desire to receive an alert when a certain condition relating to a welding arc 26 is met. For example, the welding operator 18 may desire to receive an alert when a target (e.g., predetermined) value for cumulative welding arc 26 duration, a welding arc 26 duration for a single welding arc 26, or cumulative welding arc 26 count is reached, not reached, or exceeded. The welding operator 18 may receive the alert visually (e.g., via the display 44) or audibly (e.g., via the audio device 36). Furthermore, the welding operator 18 may receive the alert while a welding operation is being performed, or after the welding operation is performed. In certain embodiments, such as production applications, the alert may notify the welding operator 18 that too few or too many welds have been made for a particular part, thereby providing guidance for improving quality control. In other embodiments, such as training applications, the alert may notify a welding operator 18 being trained that the welding arc 26 duration for a weld did not reach a target value. This could indicate to the operator 18 that the weld travel speed was either too fast or too slow. During training, normal, minimum, and maximum welding arc 26 durations may be provided to the operator 18. In certain embodiments relating to maintenance, an alert may be configured to notify the welding operator 18 that component (e.g., a protective cover lens) of the welding helmet assembly 20 needs to be replaced. In other embodiments, any suitable alert, such as those relating to production, training, and/or maintenance may be provided to the welding operator 18. In some embodiments, alerts may be provided to a remote device using a wired or wireless connection.

Accordingly, the welding helmet assembly 20 may include a wireless communication device 46 (e.g., transmitter) to allow the helmet 20 to communicate with other devices. The welding helmet assembly 20 may use the wireless communication device 46 to transmit welding arc 26 data for storage on another device, such as a computer, tablet, Smartphone, or heads-up display. The wireless communication device 46 may communicate using any suitable wireless interface, such as Wi-Fi, Bluetooth, ZigBee, wireless USB, cellular, and so forth. In certain embodiments, multiple welding helmet assemblies 20 may wirelessly transmit welding arc 26 data (e.g., the duration of each welding arc 26) to a remote device where the data can be monitored and analyzed. In such an embodiment, a supervisor, a manager, and/or an instructor may use the data to monitor productivity, efficiency, and/or techniques of welding operators 18. As will be appreciated, the wireless communication device 46 may be used to receive inputs, such as settings for the welding helmet assembly 20, resetting welding data (e.g., total welding duration, total welding counts, etc.), and so forth.

As discussed, the signals provided by the various inputs 32, 34, 36, 38, and 40 may be monitored by the control circuitry 30, as illustrated by a control configuration 48 in FIG. 3. For example, in response to a signal from the optical sensors 38 indicating that the welding arc 26 has been lit, the control circuitry 30 may send a command to the lens assembly 24 to darken the lens. In another embodiment, a signal from the automatic adjustment interface 34 may initialize the automatic sensitivity adjustment. In addition, the control circuitry 30 may be configured to give priority to one input over another. For example, to ensure that the lens is darkened when the welding arc 26 is present, the control circuitry 30 may send a command to the lens assembly 24 to darken the lens even if the last audible command to the audio device 36 was to clear the lens. Similarly, to prevent inadvertent clearing of the lens during welding, the control circuitry 30 may not respond to command signals to clear the lens while the optical sensors 38 detect the welding arc 26. As illustrated, a user interface 50 of the welding helmet assembly 20 may include the inputs 32 and 34.

The resettable total duration of the welding arc 26, as discussed above, may function similarly to a trip meter (e.g., odometer) in a car. Specifically, the resettable total duration of the welding arc 26 may keep track of the amount of welding performed since the last time it was reset. It does this by keeping track of data from the arc detection system 31 and calculating the total amount of time that the welding arc 26 is detected. At any point in time, the operator 18 may reset the resettable total duration of the welding arc 26 back to zero. This allows a welding operator 18 to keep track of their welding activity over a certain period of time, such as a day, week, month, or while working on a specific welding application. As will be appreciated, in welding application where supervisors desire to monitor the welding arc 26 data of the operator 18 (e.g., employee), the welding helmet assembly 20 and/or the lens assembly 24 may include a security feature 33 that inhibits resettable data (e.g., the resettable total duration of the welding arc 26) from being reset to zero without authentication (e.g., via a password, fingerprint, RFID device, barcode, Bluetooth communication, card reader, key sequence, key, etc.).

The date and time of the last reset may be stored in the storage device 42 so the user can compare the resettable total duration of the welding arc 26 value to the total amount of lapsed time that value corresponds to. The time of last reset may be displayed directly (e.g., 7:30 a.m. Mar. 5, 2012) or relative to the current time (e.g., 3 days, 14 hours, 15 seconds since last reset). Similarly to a non-resettable odometer in a car, a non-resettable total duration of the welding arc 26 may also tracked over the life of the lens assembly 24 and/or the welding helmet assembly 20. The non-resettable total number of welding arcs 26 may also be permanently tracked. In certain embodiments, such non-resettable data may be used to validate an amount of use of the lens assembly 24 and/or the welding helmet assembly 20 (e.g., for warranty claims).

The duration of the previous welding arc 26 may also be stored in the storage device 42 and available for display. While a total duration of the welding arc 26 may keep track of the cumulative duration of welding arcs 26 for a particular application, the duration of each individual welding arc 26 may also be available to the operator 18 without having to reset the cumulative duration of welding arcs 26 in-between each welding arc 26. This may allow analysis of data relating to certain welding applications. It may also be useful in a weld training situation when the student is instructed on the proper travel speed of a weld. In this case, the duration of a welding arc 26 may indicate the average travel speed for a known length of weld (e.g., 12 inches).

Figure 4:
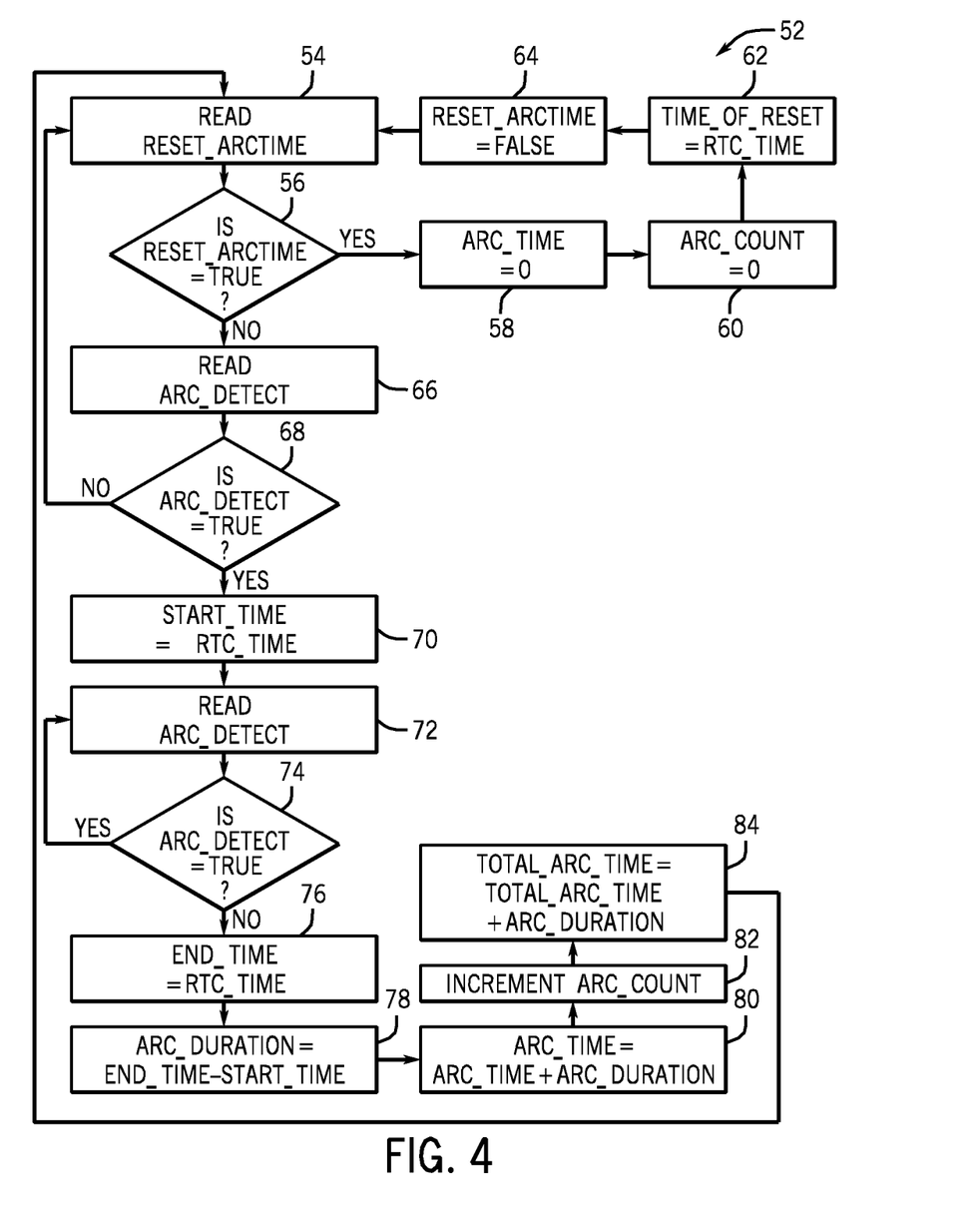
FIG. 4 is a flow chart of an embodiment of a method for determining a duration (e.g., length of time) of a welding arc in accordance with aspects of the present disclosure.

FIG. 4 is a flow chart of an embodiment of a method 52 for determining a duration (e.g., length of time) of the welding arc 26. At block 54, a RESET_ARCTIME is read by the control circuitry 30. The RESET_ARCTIME provides an indication about whether to reset an ARC_TIME (e.g., the resettable total duration of the welding arcs 26). Next, at block 56, the control circuitry 30 determines whether RESET_ARCTIME is true. If RESET_ARCTIME is true, the method 52 proceeds to block 58 and sets ARC_TIME equal to zero. At block 60, the control circuitry 30 sets ARC_COUNT (e.g., the resettable total number of welding arcs 26 since a reset of the resettable total duration of the welding arcs 26) to zero. Next, at block 62, the control circuitry 30 sets TIME_OF_RESET (e.g., the time of the last reset) to RTC_TIME (e.g., the current time). Then, at block 64, the control circuitry 30 sets RESET_ARCTIME to false.

If, at block 56, RESET_ARCTIME is false, the method 52 proceeds to block 66 where ARC_DETECT (e.g., the arc detection system 31 has detected a welding arc 26) is read. Next, at block 68, the control circuitry 30 determines whether ARC_DETECT is true. If ARC_DETECT is false, the method 52 returns to block 54. However, if ARC_DETECT is true, the method 52 moves to block 70. Then, at block 70, the control circuitry 30 sets START_TIME (e.g., the time a welding arc 26 starts) to RTC_TIME.

The method 52 proceeds to block 72 where ARC_DETECT is again read. Next, at block 74, the control circuitry 30 determines whether ARC_DETECT is true. If ARC_DETECT is true, the method 52 returns to block 72. However, if ARC_DETECT is false, the method 52 moves to block 76. Then, at block 76, the control circuitry 30 sets END_TIME (e.g., the time a welding arc 26 ends) to RTC_TIME.

At block 78, the control circuitry 30 calculates ARC_DURATION (e.g., the duration of the welding arc 26) by subtracting START_TIME from END_TIME (e.g., END_TIME−START_TIME). Next, at block 80, the control circuitry 30 updates the resettable cumulative ARC_TIME by adding ARC_TIME to ARC_DURATION. Then, at block 82, the control circuitry 30 increments the ARC_COUNT (e.g., ARC_COUNT=ARC_COUNT+1). At block 84, the control circuitry 30 updates TOTAL_ARC_TIME (e.g., the non-resettable total welding arc 26 duration) by adding TOTAL_ARC_TIME to ARC_DURATION. The method then returns to block 54.

As will be appreciated, the welding arc 26 duration (e.g., single, cumulative, resettable, non-resettable) and number of welding arcs 26 may be determined using the methods and devices described herein. Using such methods and devices, a low cost way to improve productivity and/or efficiency may be obtained.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A welding helmet, comprising:
a first sensor disposed on the welding helmet and configured to detect one or more welding arcs that occur during one or more welding operations, wherein the first sensor is an optical sensor;
a second sensor disposed on the welding helmet, wherein the second sensor comprises at least one of an electromagnetic sensor configured to detect electromagnetic emissions in a non-optical wavelength range, a position sensor, an orientation sensor, a motion sensor, a location sensor, a temperature sensor, a humidity sensor, or a sound level sensor;
control circuitry configured to:
lighten or darken a lens assembly of the welding helmet based at least in part on the one or more welding arcs detected by the first sensor;
determine whether any of the one or more welding arcs detected by the first sensor are false detections based on the second sensor; and
count a number of the one or more welding arcs detected by the first sensor without including arcs identified as false detections; and
a storage device configured to store the number of the one or more welding arcs.

2. The welding helmet of claim 1, comprising a user interface having a reset feature for resetting the number of the one or more welding arcs stored on the storage device.

3. The welding helmet of claim 1, wherein the control circuitry is configured to determine a duration of the one or more welding arcs detected by the first sensor.

4. The welding helmet of claim 1, wherein the storage device is configured to store a non-resettable number of the one or more welding arcs detected by the first sensor.

5. The welding helmet of claim 1, wherein the control circuitry is configured to enable the number of the one or more welding arcs detected by the first sensor to be resettable.

6. The welding helmet of claim 1, wherein the control circuitry is configured to store at least one of a date or a time corresponding to the number of the one or more welding arcs detected by the first sensor, wherein the at least one of the date or the time provide a reference point relating to the count of the number of the one or more welding arcs.

7. The welding helmet of claim 6, wherein the reference point indicates the at least one of the date or the time when the count of the number of the one or more welding arcs was last zero.

8. The welding helmet of claim 6, wherein the reference point indicates the at least one of the date or the time when the count of the number of the one or more welding arcs was last reset.

9. The welding helmet of claim 1, wherein the control circuitry is configured to divide the number of the one or more welding arcs detected by the first sensor into subcategories, wherein the subcategories correspond to data obtained by one or more sensors.

10. The welding helmet of claim 1, wherein the control circuitry is configured to detect an orientation of the welding helmet based on a signal from the second sensor and to count the number of the one or more welding arcs detected by the first sensor based on the orientation of the welding helmet determined by the second sensor.

11. The welding helmet of claim 10, wherein the control circuitry is configured to use the orientation of the welding helmet to determine whether the one or more welding arcs are formed by an operator wearing the welding helmet.

12. A welding helmet, comprising:
   a first sensor disposed on the welding helmet and configured to detect a plurality of welding arcs that occur during one or more welding operations, wherein the first sensor is an optical sensor;
   a second sensor disposed on the welding helmet, wherein the second sensor comprises at least one of an electromagnetic sensor configured to detect electromagnetic emissions in a non-optical wavelength range, a position sensor, an orientation sensor, a motion sensor, a location sensor, a temperature sensor, a humidity sensor, or a sound level sensor;
   control circuitry configured to:
      lighten or darken a lens assembly of the welding helmet based at least in part on the plurality of welding arcs detected by the first sensor;
      determine whether any of the one or more welding arcs detected by the first sensor are false detections based on the second sensor; and
      determine a duration of each welding arc of a portion of the plurality of welding arcs detected by the first sensor; and
   a storage device configured to store a total duration of the portion of the plurality of welding arcs detected by the first sensor, wherein the total duration of the portion of the plurality of welding arcs detected by the first sensor comprises a sum of the duration of each welding arc of the portion of the plurality of welding arcs.

13. The welding helmet of claim 12, wherein the first sensor is configured to detect the plurality of welding arcs that occur during the one or more welding operations by detecting a plurality of welding arc emissions that correspond respectively to a plurality of regions of an electromagnetic spectrum.

14. The welding helmet of claim 12, wherein the second sensor comprises at least one of an accelerometer, gyroscope, or a microelectromechanical system (MEMS).

15. The welding helmet of claim 12, comprising a display device configured to display the total duration of the portion of the plurality of welding arcs detected by the first sensor.

16. The welding helmet of claim 15, wherein the display device is configured to display a duration of a previous welding arc.

17. The welding helmet of claim 15, wherein the display device is configured to display a number of the plurality of welding arcs detected by the first sensor.

18. The welding helmet of claim 12, comprising a wireless transmitter configured to transmit arc data to a remote device.

19. The welding helmet of claim 12, wherein the storage device comprises a non-volatile storage device.

20. A welding helmet, comprising:
   a first sensor disposed on the welding helmet and configured to detect one or more welding arcs that occur during one or more welding operations, wherein the first sensor is an optical sensor;
   a second sensor disposed on the welding helmet, wherein the second sensor comprises at least one of an electromagnetic sensor configured to detect electromagnetic emissions in a non-optical wavelength range, a position sensor, an orientation sensor, a motion sensor, a location sensor, a temperature sensor, a humidity sensor, or a sound level sensor;
   control circuitry configured to:
      lighten or darken a lens assembly of the welding helmet based at least in part on the one or more welding arcs detected by the first sensor;
      determine whether any of the one or more welding arcs detected by the first sensor are false detections based on the second sensor; and
      determine a resettable duration of the one or more welding arcs detected by the arc detection system without including durations of arcs identified as false detections; and
   a storage device configured to store at least one of the resettable duration of the one or more welding arcs detected by the first sensor, a first date that provides a reference point relating to when the resettable duration was last reset, a first time that provides the reference point relating to when the resettable duration was last reset, a second date that provides the reference point relating to when the resettable duration was last zero, or a second time that provides the reference point relating to when the resettable duration was last zero.

21. The welding helmet of claim 20, comprising a security feature that inhibits the resettable duration of the one or more welding arcs from being reset without authentication.

22. The welding helmet of claim 20, wherein the storage device comprises a non-volatile storage device.

* * * * *